United States Patent [19]

Dedo

[11] Patent Number: 4,479,490
[45] Date of Patent: Oct. 30, 1984

[54] CAST PADDING

[76] Inventor: Richard G. Dedo, 175 Denise Dr., Hillsborough, Calif. 94010

[21] Appl. No.: 897,231

[22] Filed: Apr. 17, 1978

[51] Int. Cl.³ .............................................. A61F 5/04
[52] U.S. Cl. .................................. 128/89 R; 128/91 R
[58] Field of Search ...................... 128/77, 82, 83, 89, 128/90, 91, 156, 157; 273/165, 166; 2/159

[56] References Cited

U.S. PATENT DOCUMENTS

| | | | |
|---|---|---|---|
| 723,348 | 3/1903 | Wilkens | 2/159 |
| 1,845,630 | 2/1932 | Scholl | 128/156 |
| 3,040,740 | 6/1962 | Parker | 128/83 |
| 3,097,644 | 7/1963 | Parker | 128/89 R |
| 3,882,857 | 5/1975 | Woodall | 128/90 |
| 4,076,019 | 2/1978 | Sain | 128/83 |
| 4,240,415 | 12/1980 | Wartman | 128/90 |

FOREIGN PATENT DOCUMENTS 579907 9/1976 Switzerland ...................... 128/89 R Primary Examiner—Benjamin R. Padgett
Assistant Examiner—T. J. Wallen
Attorney, Agent, or Firm—Powell L. Sprunger

[57] ABSTRACT

Cast padding for use in forming a cast on a patient's extremity comprising, an elongated sleeve having a cavity and an opening communicating with the cavity. The sleeve has an outwardly turned edge extending peripherally around the opening against which plaster is wrapped during formation of the cast. The padding may also have an inner sleeve of stretchable fabric having an end section extending past the opening for placement around the edge into the plaster.

29 Claims, 12 Drawing Figures

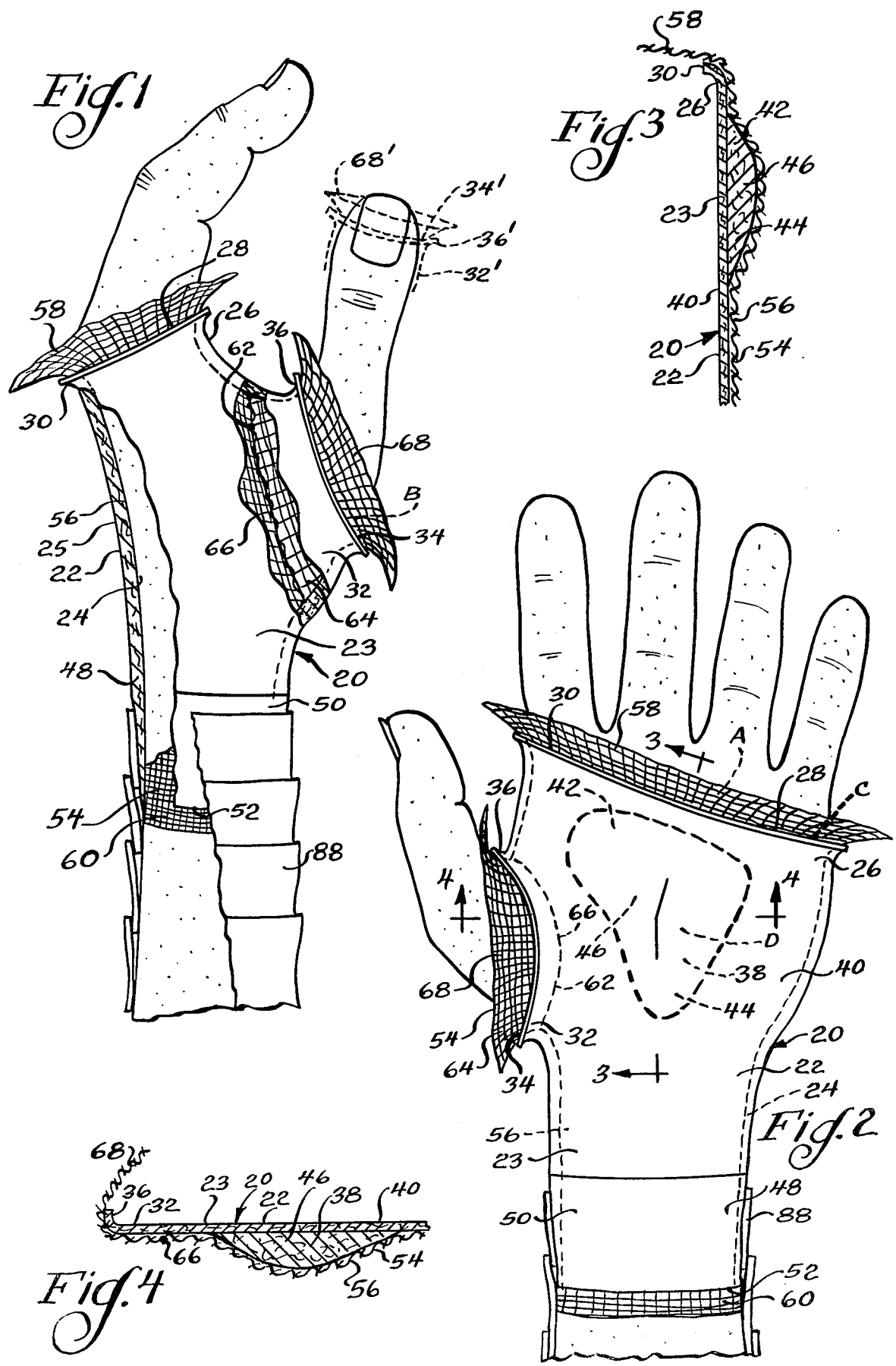

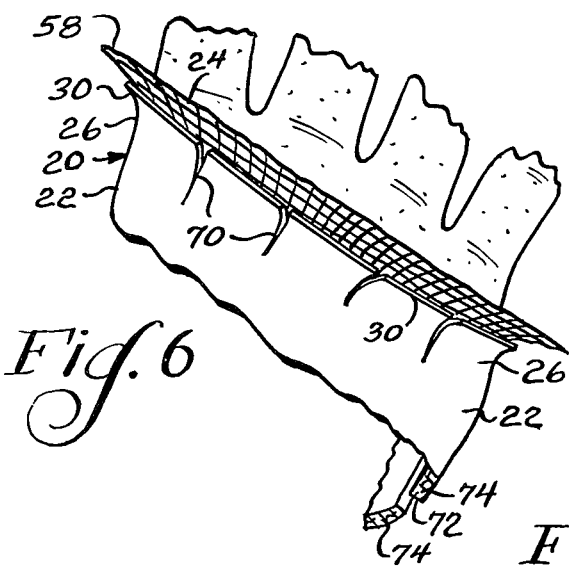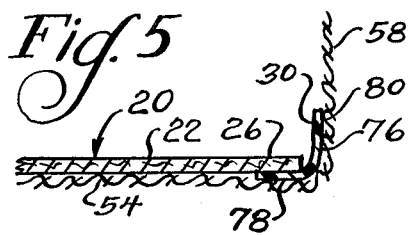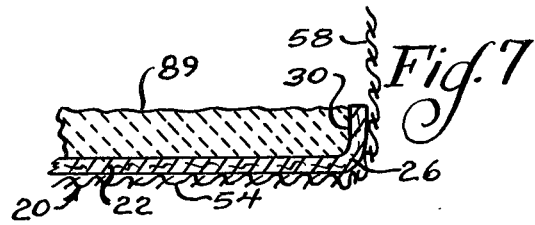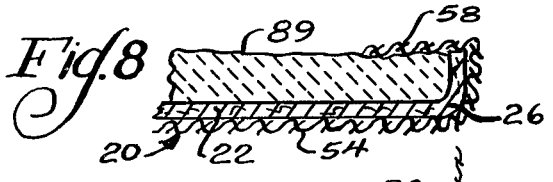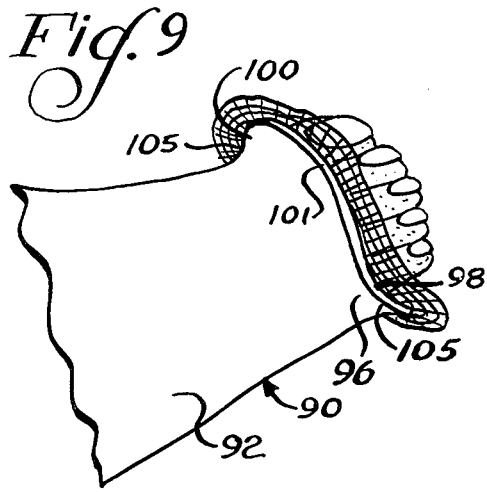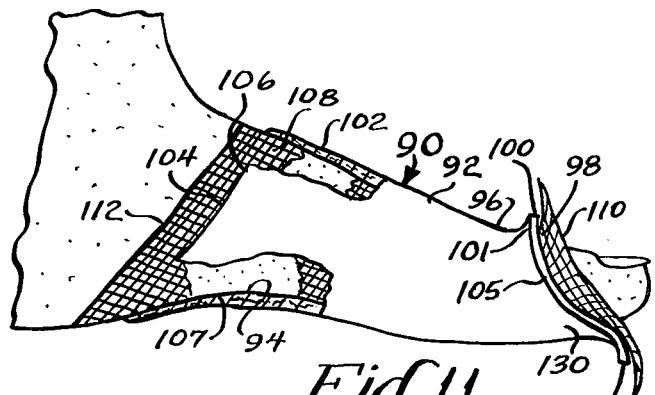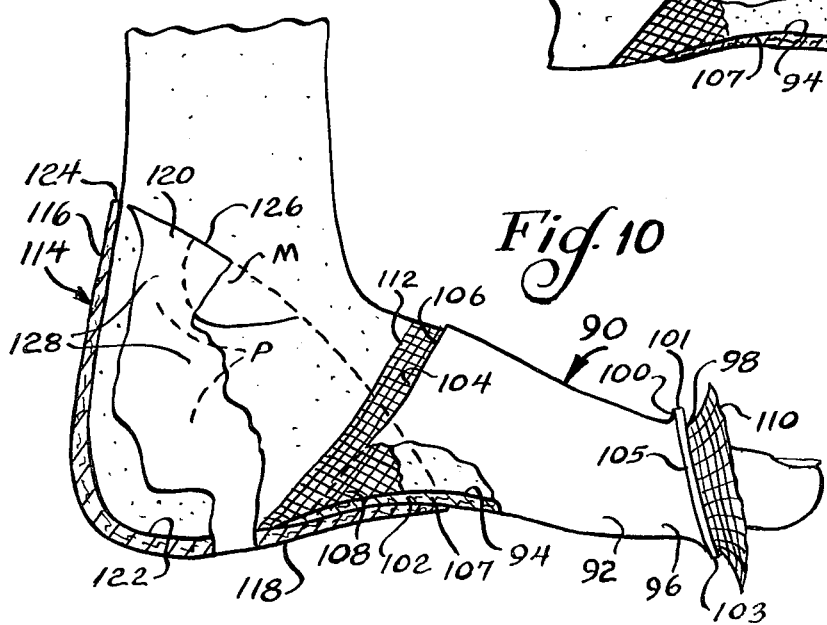

CAST PADDING

BACKGROUND OF THE INVENTION

The present invention relates to casts, and more particularly to padding for such casts.

Fairly standard procedures have been used by physicians for many years to form a cast on a patient's extremity. Such procedures have been commonly accepted with little afterthought, since there have been few significant advances in the field for a long time which would present viable alternatives. However, as discussed below, the current practice in such matters is deficient in many respects.

Thus, in the case of an arm cast, a sleeve of tubular knit, two-way stretch material, termed stockinette, is cut to length for placement over the patient's arm and hand, and an opening is cut in a side of the sleeve to receive the patient's thumb. The stockinette material defines the inside of the finished cast to provide a comfortable surface for the patient. Next, an elongated strip of sheet wadding or cast padding, which may be hereinafter termed "wadding", is wound in a helical and circular fashion about the patient's arm and hand over the stockinette material. Typically, the wadding may be wrapped in about three layers, and both the stockinette material and wadding initially extend beyond the desired distal border of the cast. The wrapped sheet wadding provides padding for the patient beneath plaster of the finished cast. However, when the wadding is wrapped about the patient's thumb, two unwrapped triangular regions frequently remain open on the front and back of the hand, termed the "intern's triangle", due to the difficulty of wrapping the wadding in this region of the hand. Further, the stockinette material does not extend along the thumb.

An elongated strip of plaster is then wrapped over the sheet wadding to form the outer part of the cast. At this time, a number of difficulties arise in the procedure. First, the plaster is permitted to contact the patient's skin through the intern's triangles formed by the wadding, resulting in discomfort and possible cutting of the skin as the patient moves his thumb in the cast during healing. Second, as the plaster is wrapped about the patient's thumb, the plaster itself may form open intern's triangles on the front and back of the hand resulting in a region of weakness in the final cast which extends between the apices of the opposed triangles.

Next, it is extremely desirable to immobilize the hand into a position of function by the cast while maintaining the transverse metacarpal arch in the hand. Generally speaking, the desired position of function may be visualized as the configuration assumed by the hand while grasping a ball the size of a small grapefruit. In this position, the hand may be immobilized for extended periods of time without contractures occurring in the fingers and thumb. Further, by maintaining the transverse metacarpal arch, the thumb is placed into a position opposing the little finger to prevent loss of function between the fingers and thumb. However, in order to accomplish this result in the past, it has been necessary for the physician to depress the plaster in the palm as it sets by applying continual pressure with the thumb against the wet plaster into the palmar depression or recess, i.e., the low area of the hand intermediate the group of muscles at the base of the thumb (thenar eminence) and the eminence proximal the base of the little finger (hypothenar eminence). When the cast finally sets, a depression of the cast is formed in the palmar recess to maintain the transverse arch, but at the cost of time and inconvenience to the physician.

Further, as the plaster is wrapped, the plaster layers form a tapered or feathered distal end which must be removed from the cast, since the end would otherwise break apart during use of the cast. Hence, the physician must wait until the cast sets, and then trim the plaster and sheet wadding generally along the location of the distal palmar crease in the hand. Next, the physician must obtain additional wet plaster, place it over the tacky plaster adjacent the distal trimmed edge, turn a distal end section of the stockinette material over onto newly wet plaster, and place further wet plaster over the turned end section of the stockinette material in order to finish the distal end of the cast. It is apparent that such a procedure causes a great deal of inconvenience to the physician accompanied by loss of time. Even when trimmed, the cast may be thinner than desired at the distal end. Further, it is noted that the stockinette material does not extend along the thumb, which precludes finishing of the plaster around the thumb in this manner. Hence, the wadding may hang out of the cast in this area, and due to a natural tendency for some patients to pull out the wadding, the cast may eventually become loose.

Similar procedures are utilized to form a cast on the patient's foot. In particular, it is necessary to trim and finish the distal end of the cast. In certain instances, it is necessary to utilize an insert below the toes to form a toe plate for the cast which results in difficulty during formation of the cast. Further, it is desirable to protect the heel area by padding without an excessive amount of material above the ankle which may result during wrapping of the heel, in addition to fitting the recesses in the foot posterior the opposed malleolii and also protect the malleolii.

SUMMARY OF THE INVENTION

A principal feature of the present invention is the provision of improved cast padding of simplified construction for use in forming a cast on a patient's extremity.

In one form, the padding comprises an elongated sleeve of flexible padding material defining a cavity to receive a patient's hand. The sleeve has a distal portion defining a distal opening communicating with the cavity to receive the patient's fingers, with the distal portion having an outwardly turned edge extending peripherally around the distal opening for placement adjacent the distal palmar crease of the patient's hand. The sleeve has a lateral portion defining a lateral opening communicating with the cavity to receive the patient's thumb, with the lateral portion having an outwardly turned edge extending peripherally around the lateral opening. The padding has an inner longitudinal tubular layer of stretchable fabric extending through the sleeve, with the layer having a lateral opening to receive the patient's thumb, and a distal end section extending past the distal opening. The padding has a lateral tubular layer of stretchable fabric extending from the opening of the longitudinal layer through the lateral opening, with the lateral layer including an outer end section extending past the lateral opening.

In another form of the invention, the padding comprises, an elongated sleeve of padding material having a cavity to receive the patient's foot, and a distal portion defining a distal opening communicating with the cavity. The distal portion has an outwardly turned edge extending peripherally around the distal opening.

A feature of the invention is that the padding eliminates the need for fitting stockinette material around the hand or the distal portion of the foot.

Another feature of the invention is that the padding eliminates the necessity of wrapping wadding around the hand and distal portion of the foot.

Still another feature of the invention is that the hand padding fills the region adjacent the thumb on the front and back of the hand, and thus protects the hand in this region from the plaster of the cast.

Yet another feature of the invention is that the outwardly turned distal edges of the hand and foot padding provide a barrier against which the plaster may be wrapped.

Thus, a feature of the invention is that the plaster may be applied in uniform thickness along the length of the padding.

Still another feature of the invention is that the hand and foot padding eliminates the necessity of trimming the distal end of the plaster and wadding during formation of the cast.

A further feature of the invention is that the plaster may be wrapped to the outwardly turned edge of the lateral hand padding portion.

Thus, a feature of the invention is that the padding eliminates weak spots in the cast adjacent the thumb on the front and back of the hand.

Still another feature of the invention is that the outer sections of the inner layer may be turned over the plaster at the distal ends of the hand and foot padding and the lateral portion of the hand padding.

Thus, another feature of the invention is that the padding facilitates finishing the cast without the necessity of obtaining additional plaster for placement over an end of stockinette material in the cast.

A further feature of the invention is the provision of a thickened region of the hand padding to substantially fill the palmar depression in the hand.

Another feature of the invention is that the thickened region maintains the transverse metacarpal arch without the necessity of applying pressure to the plaster over the palmar depression while the plaster sets.

Thus, a further feature of the invention is that the hand padding automatically immobilizes the hand in a position of function to promote healing.

Still another feature of the invention is that the foot padding may include a lower end portion extending beneath the patient's toes.

A feature of the present invention is that the foot padding facilitates the formation of a toe plate for the cast without the necessity of inserts or difficult wrapping techniques.

Still another feature of the invention is the provision of a pad having a recess to receive the heel in order to facilitate formation of the cast and enhance protection to the foot during use of the cast.

Further features will become more fully apparent in the following description of the embodiments of this invention and from the appended claims.

DESCRIPTION OF THE DRAWINGS

In the drawings:

FIG. 1 is an elevational view, partly broken away, of a cast padding for the hand of the present invention;

FIG. 2 is a front plan view of the padding of FIG. 1;

FIG. 3 is a fragmentary sectional view taken substantially as indicated along the line 3—3 of FIG. 2;

FIG. 4 is a fragmentary sectional view taken substantially as indicated along the line 4—4 of FIG. 2;

FIG. 5 is a fragmentary sectional view of another embodiment of the padding of the present invention;

FIG. 6 is a fragmentary perspective view of another embodiment of the padding of the present invention;

FIGS. 7 and 8 are fragmentary sectional views illustrating use of the padding during formation of a cast;

FIG. 9 is a fragmentary perspective view of a cast padding for the foot according to the present invention;

FIG. 10 is a fragmentary elevational view of the padding of FIG. 9 and a cast padding for placement over the patient's heel; and FIG. 11 is an elevational view, partly broken away, of another embodiment of a cast padding for the foot according to the present invention.

DESCRIPTION OF THE PREFERRED EMBODIMENTS

Referring now to FIGS. 1-4, there is shown a cast padding generally designated 20 having an elongated sleeve 22 of a flexible padding material defining a cavity 24 to receive the patient's hand. The sleeve 22 has an elongated tubular central section 23 including a palmar portion 40 for covering the palm, and a back portion 25, with the sleeve 22 having a distal portion 26 defining a distal opening 28 to receive the patient's fingers. As shown, the distal portion 26 has an outwardly turned end or edge 30 extending peripherally around the opening 28 at a location adjacent the distal palmar crease C of the patient's hand. The sleeve 22 also has a lateral portion 32 extending outwardly from the central section 23 and defining a lateral opening 34 at an outer end of the lateral portion 32 communicating with the cavity 24. The lateral portion 32 has an outwardly turned end or edge 36 extending peripherally around the lateral opening 34. In one form, the edge 36 of the lateral portion 32 is located adjacent the base B of the first metacarpal of the patient's hand. In an alternative form for a navicular cast, as shown in dotted lines in FIG. 1, the edge 36' of the lateral portion 32' is located adjacent the outer or distal end of the patient's thumb, such that the lateral portion 32' covers a substantial portion of the thumb.

With reference to FIGS. 2-4, the cast padding 20 has an inner pad 38 defining a region of increased thickness in the palmar portion 40 of the sleeve 22. The pad 38 has a tapered distal portion 42 of enlarged width, a tapered proximal portion 44 of reduced width, and a central portion 46 of increased thickness intermediate the distal portion 42 and proximal portion 44. The pad 38 has a size and shape to substantially fill the palmar recess or depression D, i.e., the low area of the hand intermediate the group of muscles at the base of the thumb (thenar eminence) and the eminence proximal the base of the little finger (hypothenar eminence), when the padding 20 is positioned on the hand.

With reference to FIGS. 1 and 2, the cast padding 20 has a proximal portion 48 located proximal the thumb in the region of the wrist. In a preferred form, as shown, the proximal portion 48 has a proximal end 50 which is tapered toward a proximal edge 52 of the sleeve 22 for a purpose which will be described below.

With reference to FIGS. 1-4, the padding 20 has an inner glove member 54 of open-mesh, two-way stretchable fabric, such as a material known in the art as a tubular knit stockinette material. The glove member 54 has an elongated inner sleeve 56 for placement over the wrist and hand, with the sleeve 56 having a distal end section 58 extending from the cavity 24 past the opening 28 and having a sufficient length for placement over an outer surface of the cast, and with the sleeve 56 having a proximal section 60 which may extend past the proximal edge 52 of the sleeve 22. The sleeve 56 of stretchable fabric has a side opening 62 to receive the patient's thumb. The glove member 54 also has a lateral tubular section 64 which may be joined to the sleeve 56 around the opening 62 by any suitable means, such as a line 66 of stitching. As shown, the lateral section 64 extends from the opening 62 through the lateral portion 32 of the sleeve 22, and extends from the cavity 24 outside the lateral opening 34, with the lateral section 64 having an outer end section 68 located outside the opening 34 and having a sufficient length for placement over an outer surface of the cast. In one form, the glove member 54 and sleeve 22 may be supplied separately to the physician, such that the physician first positions the glove member 54 over the hand, after which the sleeve 22 is placed over the glove member 54. In an alternative form, the glove member may be positioned in the cavity 24 of the sleeve 22 as supplied to the physician, such that the glove member 54 and sleeve 22 may be simultaneously positioned on the hand. In a preferred form, the glove member 54 may be secured to an inner surface of the sleeve 22, such that the glove member 54 is retained within the cavity 24 of the sleeve 22. Further, if desired, the juncture between the sleeve 56 and lateral section 64 around the opening 62 may be established by bonding the components of the glove member to the sleeve 22.

The sleeve 22 may be constructed of any suitable porous material which permits breathing through the sleeve during prolonged use of the cast, such as an orthopedic felt style S-513 sold by Southeastern Felt and Supply Corporation, Concord, N.C. In one form, the material for the sleeve 22 may have a thickness of approximately ⅛ inch to ¼ inch, and the material may be treated in the region of the edges 30 and 36 for slightly greater firmness, such as by starch, if desired. In one form, the selected material may be elastic in a circumferential direction to permit slight adjustment of the sleeve 22 to the patient's hand. In an alternative form, with reference to FIG. 6, the sleeve 22 may have a plurality of spaced longitudinal slits 70 extending proximally from the distal edge 30 to permit expansion of the sleeve 22 in the distal portion 26 of the sleeve 22. Further, as shown in FIG. 6, the sleeve 22 may have a longitudinal slit 72 extending the length of the sleeve 22, such that the sleeve 22 may be placed over the hand between opposed side edges 74 of the sleeve defining the slit 72.

In another form of the invention, as shown in FIG. 5, the padding 20 may have a sheet 76 of suitable material, preferably an elastic material, with the sheet 76 having an inner annular section 78 secured to the distal portion 26 of the sleeve 22, and an outwardly turned end section 80 defining the distal edge 30 peripherally around the distal sleeve opening. Of course, the same structure may be utilized around the lateral opening adjacent the thumb. Further, the sleeve may comprise a generally tubular padding member and a separate sheet 76 with a turned edge which are placed together at the time of use on the extremity.

With reference to FIG. 12, in a further form of the invention, the sleeve 22 may be constructed of open-cell foam material, such as urethane foam, throughout a substantial portion of the sleeve 22 to permit breathing of the padding 20 during use of the cast. Further, the foam padding 20 may have an outwardly turned section 82 defining the edge 30, with the section 82 having opposed densified layers 84 defining the opposed surfaces of the section 82 to provide a resilient and relatively firm edge for the padding 20. A similar structure of densified layers may be formed for the lateral edge 36 adjacent the thumb. The sleeve may be conveniently molded to shape the foam material, and the densified layers 84 may be formed by suitable temperature control of the mold surface and molding time during molding of the sleeve 22. In one form, the glove member 54 may be insert molded onto the sleeve 22, such that the glove member 54 is retained in the foam adjacent an inner surface 86 of the sleeve 22.

In use of the padding 20, the glove member 54 and sleeve 22 are positioned on the patient's hand, with the patient's fingers projecting from the distal opening 28, and the patient's thumb projecting from the lateral opening 34. Next, an elongated strip 88 of sheet wadding may be helically wrapped over the patient's arm, as desired, and over the proximal end 50 of the sleeve 22. The tapered configuration of the sleeve proximal end 50 permits a relatively smooth juncture between the wrapped wadding strip 88 and the sleeve 22. Next, an elongated strip of plaster may be wrapped over the wrapped wadding strip 88 and over the sleeve 22. With reference to FIG. 7, the plaster strip 89 may be wrapped in one or more layers around the sleeve to the edge 30 which defines a barrier against which the plaster may be wrapped during the wrapping procedure. Of course, with reference to FIGS. 1 and 7, the lateral edge 36 also defines a barrier for the plaster during the wrapping procedure. With reference to FIG. 8, after the plaster has been wrapped about the sleeve and against the edges 30 and 36, the distal fabric section 58 may be folded over onto the outer surface of the wet plaster where it is retained when the plaster dries to finish the distal portion of the cast. Of course, with reference to FIGS. 1 and 8, the end section 68 of the glove member 54 may be folded over the wet plaster around the thumb in order to finish the lateral portion of the cast. In the case of a navicular cast, as shown in the dotted lines in FIG. 1, the plaster is conveniently wrapped to the edge 36' defined adjacent the outer end of the thumb, and the end section 68' of the glove member is folded over onto the wet plaster to finish the lateral portion of the cast over the thumb.

Thus, in accordance with the present invention, the glove member 54 eliminates the necessity of cutting and forming a tube of stockinette material at the time of placement of the cast. Further, the sleeve 22 eliminates the necessity for the physician to wrap a wadding material around the hand pursuant to formation of the cast. As shown, the sleeve 22 fills the area of the hand around the thumb, and prevents contact of the plaster against the skin in the region of the thumb in the finished cast. A uniform layer of the plaster material may be formed against the distal edge 30 of the sleeve 22, and eliminates feathering of the cast and possible weakening adjacent the distal end of the formed cast. Moreover, the sleeve 22 permits convenient wrapping of the plaster material against the lateral edge 36 in the region around the thumb to eliminate the regions of weaknesses commonly formed in prior casts on the front and back of the hand. Since the plaster strip may be conveniently wrapped against the barrier defined by the distal edge 30, the sleeve 22 also eliminates the necessity for trimming a distal end of the cast which was previously required in prior cast forming procedures after the plaster had dried. Moreover, since the padding of the invention eliminates the necessity of trimming at the distal end of the cast, the distal section 58 may be folded over and secured to the wet plaster before the plaster has dried, thus eliminating the necessity for the physician to obtain additional wet plaster for finishing the cast after trimming has taken place. Also, since the lateral section 64 of the glove member 54 extends along the thumb, the cast may be conveniently finished around the region of the thumb by folding the end section 68 of the glove member 54 back into the wet plaster in order to finish the cast around the thumb which was not previously accomplished in prior cast forming procedures. Further, with reference to FIGS. 1-4, the inner pad 38 fills the palmar depression of the hand, and maintains the transverse metacarpal arch A in the hand during the placement procedure without the necessity for the physician to apply pressure against the plaster in the palm until it dried, which was previously required. Thus, the padding 20 of the present invention automatically maintains the hand in a position of function, as best illustrated in FIG. 1, in order to place the thumb into a position opposing the little finger and maintain the arch A. In this configuration, the hand may be immobilized for extended periods of time without contractures occurring in the fingers or thumb, and the thumb and fingers may work against each other. Finally, with reference to FIG. 1, the padding 20 permits formation of a navicular cast in a greatly simplified manner, in addition to the finishing of such a cast.

In the finished cast, the inner glove member 54 provides a comfortable inner surface for the patient's skin, while the sleeve 22 forms padding beneath the plaster. Of course, the plaster wrapped around the sleeve provides a barrier for the extremity, and immobilizes the hand into a position of function in a convenient and simplified manner to promote the healing process.

With reference to FIGS. 9 and 10, there is shown a cast padding generally designated 90 having an elongated sleeve 92 defining a cavity 94 to receive the distal part of the patient's foot. The sleeve 92 has a distal portion 96 defining a distal opening 98 communicating with the cavity 94 to receive the patient's toes. As shown, the distal portion 96 has an outwardly turned edge 100 extending peripherally around the opening 98. As best shown in FIG. 10, an upper portion 101 of the edge 100 is located slightly proximal a lower portion 103 of the edge 100, with the edge 100 being located adjacent the metatarsophalangeal joint of the patient's foot proximal the toes when the sleeve 92 is placed upon the foot. The edge 100 includes opposed, inclined side portions 105 connecting the upper and lower portions 101 and 103, respectively, of the edge 100. The sleeve 92 has a proximal portion 102 which is tapered toward a proximal edge 104 of the sleeve 92 which defines a proximal opening 106 to receive the foot with the proximal portion 102 located in the region of the patient's instep when the sleeve 92 is placed on the foot. In a preferred form, as shown, the proximal edge 104 defines an acute angle relative to a lower proximal portion 107 of the sleeve.

The padding 90 also has an inner sleeve 108 of stretchable fabric received in the cavity 94. The inner sleeve 108 has a distal end section 110 extending past the distal opening 98 and having a sufficient length for placement over an outer surface of the cast. In a preferred form, as shown, the inner sleeve 108 has a proximal end 112 extending proximally past the proximal edge 104 of the sleeve 92.

The sleeve 92 may be formed from a suitable material and in a similar manner as previously-described in connection with the sleeve 22 of the padding of FIGS. 1-8, and 12. Further, the distal edge 100 may be constructed in a manner as described in connection with the padding of FIGS. 1-8, and 12. The inner sleeve 108 may be constructed from a similar material previously discussed in connection with the glove member 54 of the padding 20 of FIG. 1-8, and 12.

As shown in FIG. 10, a heel member 114 is provided having a back wall 116 with a sufficient height to cover the Achilles tendon of the patient, a lower wall 118 having a sufficient length to extend distally from the heel to a location adjacent the patient's instep, and a pair of opposed sidewalls 120 connecting the back and lower walls 116 and 118 and having a sufficient breadth to cover the opposed malleolii M of the patient's ankle. The back wall 116, lower wall 118, and opposed sidewalls 120 define a cavity 122 to receive the patient's heel, and an outer portion 124 which is tapered toward an outer edge 126 extending peripherally around the heel member 114 and cavity 122. In a preferred form, as shown, the heel member 114 and sleeve 92 overlap in the region of the patient's instep, with both of the overlapping portions being tapered to provide a smooth juncture region between the heel member 114 and sleeve 92. Further, the sidewalls 120 include a filling region 128 of increased thickness at a location P posterior and inferior the opposed malleolii. The heel member 114 may be constructed from any suitable material, such as orthopedic felt or a suitable foam, such as an open-cell urethane foam.

In use, the sleeve 92 and inner sleeve 108 of the padding 90 is placed upon the distal part of the foot, and the heel member 114 is positioned over the heel. Next, an elongated strip of wadding material may be wrapped in a helical fashion over the proximal portion of the sleeve 92, and around the heel member 114 in the region of the ankle. When wrapping of the sheet wadding has been completed, an elongated strip of plaster may be wrapped over the wadding, the heel member 114, and the sleeve 92. The plaster may be wrapped in uniform thickness about the foot against the edge 100 which defines a barrier for the plaster. After the wrapping procedure for the plaster has been completed, the end section 110 of the inner fabric sleeve 108 may be folded back and placed into the wet plaster adjacent the edge 100 in order to finish the distal end of the cast.

Thus, in accordance with the present invention the padding 90 eliminates the necessity for fitting stockinette material on the distal part of the foot, and eliminates the necessity of wrapping the distal portion of the foot with a wadding material. The padding 90 also permits formation of a uniform thickness of plaster adjacent the edge 100 at the distal end of the cast, and eliminates the necessity for trimming the cast after the plaster has dried. The padding 90 greatly simplifies placement of the plaster at the distal end of the cast which was previously encumbered by the contour of the foot along the toes about the foot. Further, the padding 90 permits the simplified finishing of the cast by folding over the fabric end section 110 into the wet plaster without the need for additional plaster required in prior procedures after trimming a distal portion of the cast.

The heel member 114 of the present invention protects the heel in a simplified manner without the necessity for wrapping an excessive amount of wadding around the heel and ankle. Further, the sidewalls 120 of the heel member 114 cover and protect the opposed malleolii beneath the plaster in the finished cast. In addition, the thickened region 128 of the sidewalls 120 fill the areas of the foot posterior the malleolii to enhance protection beneath the finished cast. Thus, the heel member 114 and padding 90 cooperate with each other to simplify placement of the cast and provide improved protection for the patient in the finished cast.

Another embodiment of the padding 90 for the foot according to the invention, is illustrated in FIG. 11, in which like reference numerals designate like parts. In this embodiment, the padding 90 has a sleeve 92 having a distal portion 96 defining a distal opening 98, and an outwardly turned edge 100 extending peripherally around the opening 98. As before, the upper portion 101 of the edge 100 is located adjacent the metatarsophalangeal joint of the patient's foot proximal the toes. However, in this embodiment, the sleeve 92 has a lower distal portion 130 extending beneath the toes, such that the lower portion of the edge 100 is located adjacent the outer or distal end of the toes. Further, as shown, the edge 100 has arcuate side portions 105 extending around the sides of the foot and connecting the upper and lower portions 101 and 103 of the edge 100. As before, the padding 90 has an inner sleeve 108 of stretchable fabric extending through the cavity 94 and having a distal end section 110 extending past the distal opening 98.

In use, the cast padding 90 of FIG. 11 may be placed upon the distal part of the foot, and, if desired, the heel member 114 discussed in connection with FIG. 10 may be placed over the heel of the patient with the end portions of the heel member 114 and cast padding 90 overlapping in the instep, as previously described. After wrapping of the wadding strip about the ankle and heel member, an elongated strip of plaster is wrapped about the foot and sleeve 92. The plaster strip may be wrapped in helical or circular manner with uniform thickness and filled to the edge 100 which defines a barrier for the plaster strip. The plaster strip may be placed in a simplified manner over the lower distal portion 130 of the sleeve 92 and against the side and lower portions 105 and 103 of the edge 100 in order to form a lower plate for the toes. In the past, inserts have been used to accomplish this result, and the prior wrapping procedure for the plaster to form the toe plate has been relatively difficult due to the contour of the patient's foot and the extended length of the cast beneath the patient's toes. Frequently, prior procedures for forming the toe plates have resulted in a relatively roughened cast at the distal end while being carried out with considerable difficulty. However, in accordance with the present invention, the plaster strip may be readily wrapped and filled to the edge 100 of the sleeve 92 both above the foot and below the toes, and the end section 110 of the inner fabric sleeve 108 may be folded back onto the wet plaster in order to finish the cast. Thus, the cast and toe plate may be formed with an improved structure and in a simplified manner through use of the cast padding of the present invention. Of course, the padding 90 of FIG. 11 provides the other advantages previously discussed in connection with the padding of FIGS. 9 and 10.

The foregoing detailed description is given for clearness of understanding only, and no unnecessary limitations should be understood therefrom, as modifications will be obvious to those skilled in the art.

I claim:

1. Cast padding for use in forming a cast on a patient's extremity comprising, elongated sleeve means of a padding material being substantially more rigid than a stockinette material and defining a cavity to receive the patient's hand, said sleeve means having a palmar portion for covering a substantial portion of the patient's palm, a distal portion defining a distal opening communicating with said cavity to receive the patient's fingers, and a lateral portion extending a distance for the sleeve means and defining a lateral opening to receive the patient's thumb, said distal portion only extending to a location adjacent the distal palmar crease, said lateral portion only extending to a location adjacent the distal end of the patient's thumb.

2. Cast padding for use in forming a cast on a patient's extremity comprising, an elongated sleeve of a padding material being substantially more rigid than a stockinette material and defining a cavity to receive the patient's hand, said sleeve having a distal portion defining a distal opening communicating with said cavity to receive the patient's fingers, said distal portion having an outwardly turned edge extending peripherally around said distal opening located for placement adjacent the distal palmar crease of the patient's hand, said sleeve having a lateral portion extending a distance from the sleeve and defining a lateral opening communicating with said cavity to receive the patient's thumb, said lateral portion having an outwardly turned edge extending peripherally around said lateral opening, with said turned edges having a sufficient length and being outwardly flared from the sleeve at a sufficient angle to wrap at least one layer of plaster against a proximal side surface of the edges, and with said edges having sufficient rigidity to maintain said flared configuration.

3. The padding of claim 2 wherein the outwardly turned edge of said lateral portion is located for placement adjacent the base of the first metacarpal of the patient's hand.

4. The padding of claim 2 wherein the outwardly turned edge of said lateral portion is located for placement adjacent the outer end of the patient's thumb.

5. The padding of claim 2 wherein said sleeve includes a region of increased thickness in a palmar portion to substantially fill the palmar depression of the patient's hand.

6. The padding of claim 2 including an inner longitudinal tubular layer of stretchable fabric extending through the sleeve, said layer having a lateral opening to receive the patient's thumb, and a distal end section extending past said distal opening and having a sufficient length for placement over an outer surface of the cast, and including a lateral tubular layer of stretchable fabric extending from the opening of said longitudinal layer through the lateral opening, said lateral layer including an outer end section having a sufficient length for placement over an outer surface of the cast.

7. Cast padding for use in forming a cast on a patient's extremity comprising, elongated sleeve means of padding material being substantially more rigid than a stockinette material and having a cavity to receive the patient's foot and a distal portion defining a distal opening communicating with said cavity to receive the patient's toes, said distal portion having an outwardly turned edge extending at least partially around said distal opening, with said turned edge having a sufficient length and being outwardly flared from the sleeve means at a sufficient angle to wrap at least one layer of plaster against a proximal side surface of the edge, with a proximal end of said sleeve means being free of a turned edge and with said edge having sufficient rigidity to maintain the flared configuration.

8. The padding of claim 7 wherein said outwardly turned edge extends peripherally around said opening, and in which an upper portion of said turned edge is located for placement adjacent the metatarso-phalangeal joint of the patient's foot.

9. The padding of claim 8 wherein a lower portion of said turned edge is located for placement adjacent the metatarso-phalangeal joint of the patient's foot.

10. The padding of claim 8 wherein a lower portion of said turned edge is located for placement adjacent a distal end of the patient's toes.

11. The padding of claim 7 wherein said sleeve means includes a proximal portion defining a proximal opening in the region of the patient's instep.

12. The padding of claim 7 including an inner sleeve of stretchable fabric received in said cavity, said inner sleeve having a distal end section extending past the distal opening and having a sufficient length for placement over an outer surface of the cast.

13. The padding of claim 12 wherein said inner sleeve includes a proximal end extending proximally from a proximal end of said sleeve means.

14. The padding of claim 7 wherein the sleeve means includes an upper outwardly turned edge adjacent said distal opening, and a lower outwardly turned edge adjacent said distal opening, said upper edge being located proximal said lower edge.

15. Cast padding for use in forming a cast on a patient's extremity comprising, a sleeve of padding material being substantially more rigid than a stockinette material and defining a cavity to receive the patient's hand, said sleeve having a lateral opening to receive the patient's thumb, a distal portion defining a distal opening communicating with said cavity to receive the patient's fingers, said distal portion having an outwardly turned edge extending at least partially around said distal opening, with said turned edge having a sufficient length and being outwardly flared from the sleeve at a sufficient angle to wrap at least one layer of plaster against a proximal side surface of the edge, with the proximal end of said sleeve being free of an outwardly turned edge and with said edge having sufficient rigidity to maintain the flared configuration.

16. Cast padding for use in forming a cast on a patient's extremity comprising, a sleeve of padding material being substantially more rigid than a stockinette material and defining a cavity to receive the patient's hand, said sleeve having a lateral portion extending a distance from the sleeve and defining a lateral opening communicating with said cavity to receive the patient's thumb, said lateral portion having an outwardly turned edge extending at least partially around said lateral opening, with said turned edge having a sufficient length and being outwardly flared from the sleeve at a sufficient angle to wrap at least one layer of plaster against the edge, and with the edge having sufficient rigidity to maintain the flared configuration.

17. Cast padding for use in forming a cast on a patient's extremity comprising, elongated sleeve means of a padding material being substantially more rigid than a stockinette material and defining a cavity to receive the patient's hand, said sleeve means having a palmar portion for covering a substantial portion of the patient's palm, a distal portion defining a distal opening communicating with said cavity to receive the patient's fingers, and a lateral portion extending a distance from the sleeve means and defining a lateral opening to receive the patient's thumb, said distal portion extending to a location adjacent the distal palmar crease, said distal portion including an outwardly turned edge extending at least partially around said distal opening.

18. The padding of claim 17 including an inner layer of stretchable fabric extending from said cavity through said distal opening, said layer having an end section distal said opening with a sufficient length for placement over an outer surface of the cast.

19. Cast padding for use in forming a cast on a patient's extremity comprising, elongated sleeve means of a padding material being substantially more rigid than a stockinette material and defining a cavity to receive the patient's hand, said sleeve means having a palmar portion for covering a substantial portion of the patient's palm, a distal portion defining a distal opening communicating with said cavity to receive the patient's fingers, and a lateral portion extending a distance from the sleeve means and defining a lateral opening to receive the patient's thumb, said distal portion extending to a location adjacent the distal palmar crease, said lateral portion extending to a location adjacent the base of the first metacarpal of the patient's hand, said lateral portion including an outwardly turned edge extending at least partially around said lateral opening.

20. The padding of claim 19 including an inner layer of stretchable fabric extending from said cavity through said lateral opening, said layer having a lateral end section outside said opening with a sufficient length for placement over an outer surface of the cast.

21. Cast padding for use in forming a cast on a patient's extremity comprising, elongated sleeve means of a padding material being substantially more rigid than a stockinette material and defining a cavity to receive the patient's hand, said sleeve means having a palmar portion for covering a substantial portion of the patient's palm, a distal portion defining a distal opening communicating with said cavity to receive the patient's fingers, and a lateral portion extending a distance from the sleeve means and defining a lateral opening to receive the patient's thumb, said distal portion extending to a location adjacent the distal palmar crease, said lateral portion extending to a location adjacent the distal end of the patient's thumb, said lateral portion including an outwardly turned edge extending at least partially around said lateral opening.

22. The padding of claim 21 including an inner layer of stretchable fabric extending from said cavity through said lateral opening, said layer having a lateral end section outside said opening with a sufficient length for placement over an outer surface of the cast.

23. Cast padding for use in forming a cast on a patient's extremity comprising, elongated sleeve means of a padding material being substantially more rigid than a stockinette material and defining a cavity to receive the patient's hand, said sleeve means having a palmar portion for covering a substantial portion of the patient's palm, a distal portion defining a distal opening communicating with said cavity to receive the patient's fingers, and a lateral portion extending a distance from the sleeve means and defining a lateral opening to receive the patient's thumb, said distal portion extending to a location adjacent the distal palmar crease, including an inner longitudinal tubular layer of stretchable fabric extending through said sleeve means, said layer including a lateral opening to receive the patient's thumb and a lateral section extending past the lateral opening of the sleeve means, and a distal end section extending a distance past said distal opening.

24. The padding of claim 23 wherein said layer includes a proximal end section extending past a proximal end of said sleeve means.

25. The padding of claim 23 including a lateral tubular layer of stretchable fabric extending from the opening of said longitudinal layer through said lateral opening, said lateral layer including an outer section extending a distance past said lateral opening.

26. The padding of claim 25 wherein said lateral and longitudinal layers are joined adjacent the opening of said longitudinal layer.

27. The padding of claim 25 wherein said lateral and longitudinal layers are secured to the sleeve means in said cavity.

28. Cast padding for use in forming a cast on a patient's extremity comprising, elongated sleeve means of a padding material being substantially more rigid than a stockinette material and defining a cavity to receive the patient's hand, said sleeve means having a palmar portion for covering a substantial portion of the patient's palm, a distal portion defining a distal opening communicating with said cavity to receive the patient's fingers, and a lateral portion extending a distance from the sleeve means and defining a lateral opening to receive the patient's thumb, said distal portion extending to a location adjacent the distal palmar crease, said palmar portion including an inner pad located for placement in the palmar recess, said pad including a tapered distal portion of enlarged width, and a tapered proximal portion of reduced width, said pad having an enlarged thickness intermediate said distal and proximal portions.

29. Cast padding for use in forming a cast on a patient's extremity comprising, a heel member of padding material having a back wall having a sufficient height to substantially cover the Achilles tendon of the patient, a lower wall having a sufficient length to extend distally to a location adjacent the patient's instep, and a pair of opposed sidewalls connecting the back wall and lower wall and having a sufficient breadth to cover the opposed malleolii of the patient's foot, said back wall, lower wall, and sidewalls defining a cavity to receive the patient's heel and an outer edge extending peripherally around the cavity, said sidewalls including a region of increased thickness posterior and inferior to the malleolii.

* * * * *